(12) United States Patent
Castan et al.

(10) Patent No.: US 12,371,647 B2
(45) Date of Patent: Jul. 29, 2025

(54) BIOREACTOR SYSTEM

(71) Applicant: Cytiva Sweden AB, Uppsala (SE)

(72) Inventors: Andreas Castan, Uppsala (SE); Ricardo A. Medronho, Rio de Janeiro (BR); Leda Castilho, Rio de Janeiro (BR); Iona Walter Bettinardi, Rio de Janeiro (BR)

(73) Assignee: Cytiva Sweden AB, Uppsala (SE)

( * ) Notice: Subject to any disclaimer, the term of this patent is extended or adjusted under 35 U.S.C. 154(b) by 919 days.

(21) Appl. No.: 17/435,436

(22) PCT Filed: Mar. 25, 2020

(86) PCT No.: PCT/EP2020/058313
§ 371 (c)(1),
(2) Date: Sep. 1, 2021

(87) PCT Pub. No.: WO2020/193613
PCT Pub. Date: Oct. 1, 2020

(65) Prior Publication Data
US 2022/0127557 A1    Apr. 28, 2022

(30) Foreign Application Priority Data

Mar. 25, 2019 (GB) .................................. 1904083

(51) Int. Cl.
*C12M 1/26* (2006.01)
*B04C 5/14* (2006.01)
(Continued)

(52) U.S. Cl.
CPC .............. *C12M 33/14* (2013.01); *B04C 5/14* (2013.01); *B04C 5/26* (2013.01); *B04C 9/00* (2013.01);
(Continued)

(58) Field of Classification Search
CPC ...... C12M 33/14; C12M 23/06; C12M 23/14; C12M 23/28; C12M 29/16; C12M 29/18;
(Continued)

(56) References Cited

U.S. PATENT DOCUMENTS 2,724,503 A * 11/1955 Fontein ..................... B04C 5/12
                                                          209/729
3,989,599 A    11/1976 Bull et al.
(Continued)

FOREIGN PATENT DOCUMENTS

CH        385170       7/1961
CN     1546641 A      11/2004
(Continued)

OTHER PUBLICATIONS

PCT International Search Report and Written Opinion for PCT/EP2020/058313 mailed Jun. 29, 2020 (12 pages).
(Continued)

*Primary Examiner* — William H. Beisner
*Assistant Examiner* — Danielle B Henkel
(74) *Attorney, Agent, or Firm* — Eversheds-Sutherland (US) LLP (57) ABSTRACT

A bioreactor system for culturing cells, comprising: —at least one bioreactor (3); and —at least one hydrocyclone (5a; 5b; 5c; 5d, 5d'; 5e) comprising: —a cell culture inlet (7) which is connected to a cell culture outlet (9) of the bioreactor (3) via a pump (11), whereby a cell culture from the bioreactor can be transferred to the hydrocyclone (5a; 5b; 5c; 5d, 5d'; 5e) when a cell culture is provided in the bioreactor, —a hydrocyclone separation part (13) into which cell culture can be introduced from the cell culture inlet (7), —a top outlet (15) through which a part of the cell culture with decreased cell concentration can be transferred after separation in the hydrocyclone separation pan (13); and —a
(Continued)

bottom outlet (17) through which a pan of the cell culture with increased cell concentration can be transferred after separation in the hydrocyclone separation part (13), wherein said bottom outlet (17) of the hydrocyclone (5a; 5b; 5c; 5d, 5d'; 5e) is provided in a position such that when the bioreactor system is used for culturing cells the bottom outlet (17) is in connection with a headspace (21) of the bioreactor (3) and wherein said bottom outlet (17) is provided such that the bottom outlet (17) has a free space around it such that a cell culture transferred out form the bottom outlet (17) is allowed to freely discharge around the bottom outlet.

10 Claims, 4 Drawing Sheets (51) Int. Cl.
*B04C 5/26* (2006.01)
*B04C 9/00* (2006.01)
*C12M 1/00* (2006.01)
*C12M 1/12* (2006.01)

(52) U.S. Cl.
CPC ............ *C12M 23/06* (2013.01); *C12M 23/14* (2013.01); *C12M 23/28* (2013.01); *C12M 29/16* (2013.01); *B04C 2009/002* (2013.01)

(58) Field of Classification Search
CPC . C12M 33/10; B04C 5/14; B04C 5/26; B04C 9/00; B04C 2009/002
See application file for complete search history.

(56) References Cited

U.S. PATENT DOCUMENTS

| | | | |
|---|---|---|---|
| 4,280,902 A | 7/1981 | Jacobsen et al. | |
| 2001/0002009 A1* | 5/2001 | Gil | B04C 5/14 |
| | | | 210/512.1 |
| 2003/0166269 A1 | 9/2003 | Deckwer et al. | |
| 2007/0039855 A1 | 2/2007 | Wagner et al. | |
| 2007/0216500 A1* | 9/2007 | Bart | B04C 5/15 |
| | | | 333/248 |
| 2009/0042253 A1 | 2/2009 | Hiller | |
| 2010/0069217 A1 | 3/2010 | Aoki et al. | |
| 2010/0210003 A1* | 8/2010 | King | C12M 23/06 |
| | | | 435/257.1 |
| 2013/0098836 A1* | 4/2013 | Penny | B01D 17/10 |
| | | | 210/85 |
| 2017/0333815 A1 | 11/2017 | Kompala | |

FOREIGN PATENT DOCUMENTS

| | | |
|---|---|---|
| CN | 101014402 A | 8/2007 |
| CN | 101524672 A | 9/2009 |
| CN | 104160013 A | 11/2014 |
| CN | 106457302 A | 2/2017 |
| DE | 2020004019123 U1 | 3/2005 |
| EP | 1280885 A1 | 2/2003 |
| FR | 2241330 A1 | 3/1975 |

OTHER PUBLICATIONS

Great Britain Search Report for GB Application No. 1904083.1 mailed Sep. 19, 2019 (6 pages).
Office Action Issued in Chinese Patent Application No. 202080023918.1, dated Aug. 19, 2022 with English Translation. (19 pages).
European Patent Office Communication Issued in European Patent Application No. 20714566.2, mailed on Sep. 27, 2022 (19 pages).

* cited by examiner

BIOREACTOR SYSTEM

CROSS REFERENCE TO RELATED APPLICATIONS

This application claims the priority benefit of PCT/EP2020/058313, filed on Mar. 25, 2020, which claims the benefit of Great Britain Application No. 1904083.1, filed 25 Mar. 2019, the entire contents of which are incorporated by reference herein.

TECHNICAL FIELD OF THE INVENTION

The present invention relates to a bioreactor system, a hydrocyclone and a method for culturing cells.

BACKGROUND

In methods and systems for culturing cells there is a need to separate cells from medium. Conventional methods are centrifugation, microfiltration and settling. In U.S. Pat. No. 6,878,545, hereby incorporated by reference in its entirety, the use of a hydrocyclone is described for the separation of cells. A suspension of decreased cell concentration is collected at a top run-off outlet of the hydrocyclone and a suspension of increased cell concentration is collected at a bottom run-off outlet of the hydrocyclone. A problem is that there are still cells left in the suspension which is collected at the top run-off outlet.

SUMMARY

An object of the invention is to provide an improved method and system for separating cells with one or more hydrocyclones in a bioreactor system.

A particular object is to improve the cell separation efficiency in the hydrocyclone(s).

This is achieved by a bioreactor system, a hydrocyclone and a method according to the independent claims.

According to one aspect of the invention a bioreactor system for culturing cells is provided, comprising:
  at least one bioreactor; and
  at least one hydrocyclone comprising:
  a cell culture inlet which is connected to a cell culture outlet of the bioreactor via a pump, whereby a cell culture from the bioreactor can be transferred to the hydrocyclone when a cell culture is provided in the bioreactor;
  a hydrocyclone separation part into which cell culture can be introduced from the cell culture inlet,
  a top outlet through which a part of the cell culture with decreased cell concentration can be transferred after separation in the hydrocyclone separation part; and
  a bottom outlet through which a part of the cell culture with increased cell concentration can be transferred after separation in the hydrocyclone separation part, wherein said bottom outlet of the hydrocyclone is provided in a position such that when the bioreactor system is used for culturing cells the bottom outlet is in connection with a headspace of the bioreactor and wherein said bottom outlet is provided such that the bottom outlet has a free space around it such that a cell culture transferred out form the bottom outlet is allowed to freely discharge around the bottom outlet.

According to another aspect of the invention a hydrocyclone configured to be connected to a bioreactor is provided, said hydrocyclone comprising:
  a cell culture inlet which is configured to be connected to a cell culture in the bioreactor via a pump, whereby cell culture from the bioreactor can be transferred to the hydrocyclone;
  a hydrocyclone separation part into which cell culture can be introduced from the cell culture inlet,
  a top outlet through which a part of the cell culture with decreased cell concentration can be transferred after separation in the hydrocyclone separation part;
  a bottom outlet through which a part of the cell culture with increased cell concentration can be transferred after separation in the hydrocyclone separation part; and
  a connection device which is provided to surround the bottom outlet of the hydrocyclone leaving a free space around it such that a cell culture transferred out form the bottom outlet is allowed to freely discharge around the bottom outlet, wherein said connection device is configured to be connected to an inlet of the bioreactor.

According to another aspect of the invention a method for culturing cells in a bioreactor system comprising at least one bioreactor and at least one hydrocyclone is provided, wherein said method comprises the steps of:
  transferring a part of a cell culture provided in the bioreactor to a cell culture inlet of the hydrocyclone;
  separating the cell culture in a hydrocyclone separation part of the hydrocyclone into which hydrocyclone separation part the cell culture is introduced from the cell culture inlet, whereby the cell culture is separated into one part of the cell culture with decreased cell concentration and one part of the cell culture with increased cell concentration;
  transferring the part of the cell culture with decreased cell concentration out from the hydrocyclone through a top outlet of the hydrocyclone; and
  freely discharging the part of the cell culture with increased cell concentration out from the hydrocyclone through a bottom outlet of the hydrocyclone, wherein said bottom outlet of the hydrocyclone is provided in connection with a headspace in the bioreactor and wherein said bottom outlet is provided such that the bottom outlet has a free space around it such that the cell culture transferred out form the bottom outlet is allowed to freely discharge around the bottom outlet.

According to another aspect of the invention a method for culturing of cells in a bioreactor system as defined above is provided.

Hereby, by providing the bottom outlet of the hydrocyclone such that the cell culture transferred out form the bottom outlet is allowed to be freely discharged around the bottom outlet there will be a decreased content of cells in the cell culture transferred out from the top outlet compared to if the bottom outlet is connected to the bioreactor with an ordinary tube which would be the normal. The reason is that if possible the flow out from the bottom outlet will tend to be discharged out in all directions, i.e. also towards the sides. When an ordinary tube is provided to the bottom outlet the discharge is restricted and a back flow upwards in the hydrocyclone is provided. Hereby, a backpressure will be created into the hydrocyclone if a traditional tube connection is provided to the bottom outlet. By the present invention, where the flow out from the bottom outlet is allowed to be freely discharged such a back flow is avoided and the waste of cells in the bioreactor system can be decreased.

In one embodiment of the invention said bottom outlet is provided such that the bottom outlet has a free space of at least 1 cm radially around it.

In one embodiment of the invention the hydrocyclone is integrated with the bioreactor such that the bottom outlet of the hydrocyclone is provided directly in the headspace of the bioreactor when the bioreactor system is used for culturing cells.

In one embodiment of the invention the hydrocyclone comprises a connection device which is provided to surround the bottom outlet of the hydrocyclone leaving a free space around it, wherein said connection device is connected to an inlet of the bioreactor, optionally via an aseptic connector.

In one embodiment of the invention said connection device is a tubular part connected to the hydrocyclone symmetrically around the bottom outlet, wherein said tubular part has an inner diameter of at least 2 cm.

In one embodiment of the invention the bioreactor is a flexible bag and the hydrocyclone is produced from plastic and wherein at least the bioreactor, the hydrocyclone and a single-use part of the pump are provided as single-use components of the bioreactor system, optionally as a pre-sterilized single-use package.

In one embodiment of the invention the hydrocyclone is provided inside the bioreactor and the top outlet of the hydrocyclone is connected to a port in a wall of the bioreactor.

In one embodiment of the invention the bottom outlet of the hydrocyclone is provided pointing or extending into the bioreactor whereby the hydrocyclone is integrated in a side wall of the bioreactor.

In one embodiment of the invention the bioreactor system comprises at least two connected hydrocyclones, wherein the top outlet(s) of one or more first hydrocyclone(s) is connected to a cell culture inlet of a second hydrocyclone and wherein all the hydrocyclones are positioned such that their bottom outlets are provided in connection with the headspace in the bioreactor when the bioreactor system is used for culturing cells.

In one embodiment of the invention the bioreactor system further comprises a hollow fiber filter comprising an inlet connected to the top outlet of the hydrocyclone and a retentate outlet connected to the bioreactor and a permeate outlet configured for transferring a part of the cell culture with decreased cell concentration out from the bioreactor system when the bioreactor system is used for culturing cells.

DETAILED DESCRIPTION OF EMBODIMENTS

FIGS. 1-5 show schematically bioreactor systems 1a; 1b; 1c; 1d; 1e according to different embodiments of the invention. Corresponding components are given the same or corresponding reference numbers. The basic inventive idea will first be described with reference to all the different embodiments and then each embodiment will be described in more detail. The bioreactor system 1a; 1b, 1c; 1d; 1e for culturing cells according to the invention comprises at least one bioreactor 3 and at least one hydrocyclone 5a; 5b; 5c; 5d, 5d'; 5e. The hydrocyclone comprises a cell culture inlet 7 which is connected to a cell culture outlet 9 of the bioreactor 3 via a pump 11, whereby a cell culture from the bioreactor 3 can be transferred to the hydrocyclone 5a; 5b; 5c; 5d, 5d'; 5e when a cell culture is provided in the bioreactor. The hydrocyclone 5a; 5b; 5c; 5d, 5d'; 5e comprises furthermore a hydrocyclone separation part 13 into which cell culture can be introduced from the cell culture inlet 7, a top outlet 15 through which a part of the cell culture with decreased cell concentration can be transferred after separation in the hydrocyclone separation part 13 and a bottom outlet 17 through which a part of the cell culture with increased cell concentration can be transferred after separation in the hydrocyclone separation part 13. The principle of a hydrocyclone is well known and will not be described in detail here however the hydrocyclone separation part 13 comprises a conical part into which the cell culture inlet 7 directs cell culture tangentially into an upper, wider part of the conical part and the bottom outlet 17 is provided at the narrow end of the conical part.

According to the invention said bottom outlet 17 of the hydrocyclone 5a; 5b; 5c; 5d, 5d'; 5e is provided in a position such that when the bioreactor system is used for culturing cells the bottom outlet 17 is in connection with a headspace 21 of the bioreactor 3 and said bottom outlet 17 is provided such that the bottom outlet 17 has a free space around it such that a cell culture transferred out form the bottom outlet is allowed to freely discharge, such as spraying out around the bottom outlet 17. This is in contrast to prior art hydrocyclones which are connected by for example an ordinary tube for transferring an outflow from the bottom outlet. The connection of a tube to the bottom outlet for transferring a flow out from the bottom outlet will affect the separation efficiency for the hydrocyclone. This is shown and compared in FIG. 6 and will be described further below. The reason is that a tube connected directly to the bottom outlet will prevent an outflow from the bottom outlet out to the sides and create a backpressure. Hereby a back flow into the hydrocyclone is provided and the separation efficiency for the hydrocyclone is decreased.

In some embodiments of the invention said bottom outlet 17 is provided such that the bottom outlet has a free space of at least 1 cm in all directions around it, i.e. at least 1 cm radially around the bottom outlet and at least 1 cm axially below the outlet referring to the directions in the drawings. A free space around the bottom outlet 17 can be achieved by providing a connection device 31 to the hydrocyclone 5a; 5c; 5d, 5d'; 5e, which connection device 31 is provided to surround the bottom outlet 17 of the hydrocyclone leaving a free space around it. The connection device 31 can be a tubular part connected to the hydrocyclone 5a; 5c; 5d, 5d'; 5e symmetrically around the bottom outlet 17, wherein said tubular part in one embodiment of the invention can have an inner diameter of at least 2 cm. The tubular part could be a flexible or rigid tube allowing connection to an inlet 33 of the bioreactor 3, optionally via an aseptic connector 35a, 35b, which can be seen in FIG. 3. The connection device 31 can for example comprise a bellows or a telescope connection for allowing a connection to the bioreactor 3 where the bottom outlet 17 can be provided pointing or extending into the headspace 21 of the bioreactor 3. The connection device 31 can have an inner diameter which is the same as a maximum diameter of the hydrocyclone separation part 13. However the inner diameter of the connection device 31 can also be smaller, it can for example have an inner diameter which is at least ⅓ the size of the maximum diameter of the hydrocyclone separation part 13, hereby leaving a free space around the bottom outlet 17.

Figure 1:
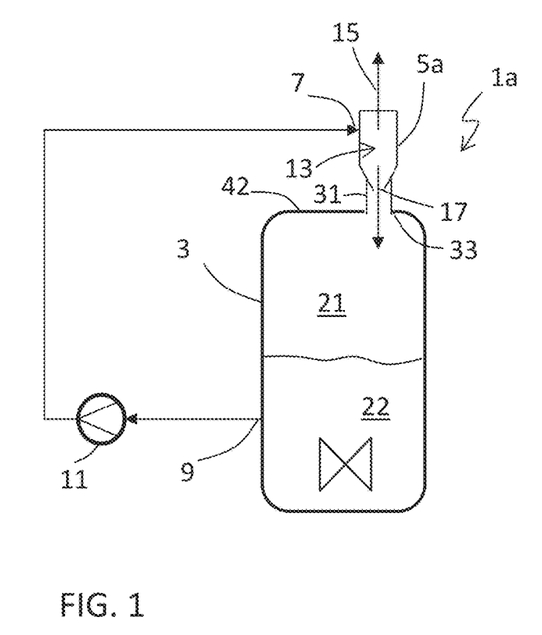
FIG. 1 shows schematically a bioreactor system according to one embodiment of the invention.
Figure 2:
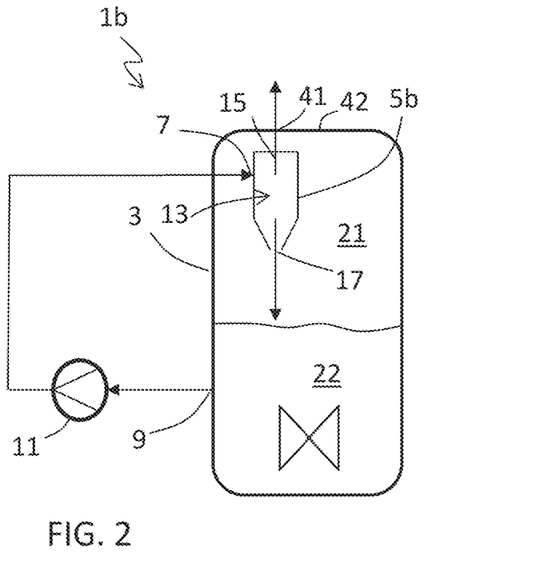
FIG. 2 shows schematically a bioreactor system according to one embodiment of the invention.

Another alternative of providing the free space around the bottom outlet 17 is to provide the hydrocyclone 5b inside the bioreactor 3 in the bioreactor system 1b as shown in FIG. 2. In this embodiment of the invention the top outlet 15 of the hydrocyclone 5b is connected to a port 41 in a wall 42 of the bioreactor 3. The bottom outlet 17 should then be provided in a position in the bioreactor 3 such that it is provided in the headspace 21 of the bioreactor 3 and not in the cell culture 22 when cell culture is provided in the bioreactor 3. Hereby a free space is provided around the bottom outlet 17 and the cell culture can freely discharge around the bottom outlet 17, such as spray out from the bottom outlet. A free space hereby means that no parts which will disturb the flow out from the bottom outlet 17 are provided closer than for example 1 cm to the bottom outlet 17. No connection needs to be provided to the bottom outlet 17 in this embodiment because the bottom outlet is provided directly in the headspace of the bioreactor. A hydrocyclone 5b as shown in FIG. 2 could also be integrated into a side wall 42 of the bioreactor 1a as shown in FIG. 1 without a separate connection device 31, i.e. an outer surface of the hydrocyclone itself can be integrated into the side wall 42 of the bioreactor 3 such that the bottom outlet 17 of the hydrocyclone is pointing or extending into the headspace 21 of the bioreactor 3.

In some embodiments of the invention, for example as shown in FIGS. 1, 2, 4 and 5, the hydrocyclone 5a, 5b, 5d, 5d', 5e is integrated with the bioreactor 3 such that the bottom outlet 17 of the hydrocyclone is provided directly in the headspace 21 of the bioreactor 3 when the bioreactor system is used for culturing cells.

Figure 4:
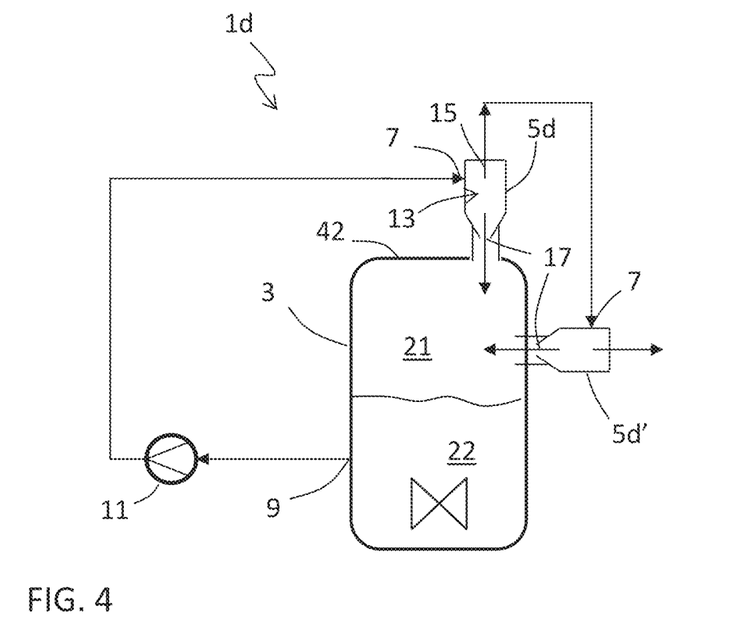
FIG. 4 shows schematically a bioreactor system according to another embodiment of the invention.
Figure 5:
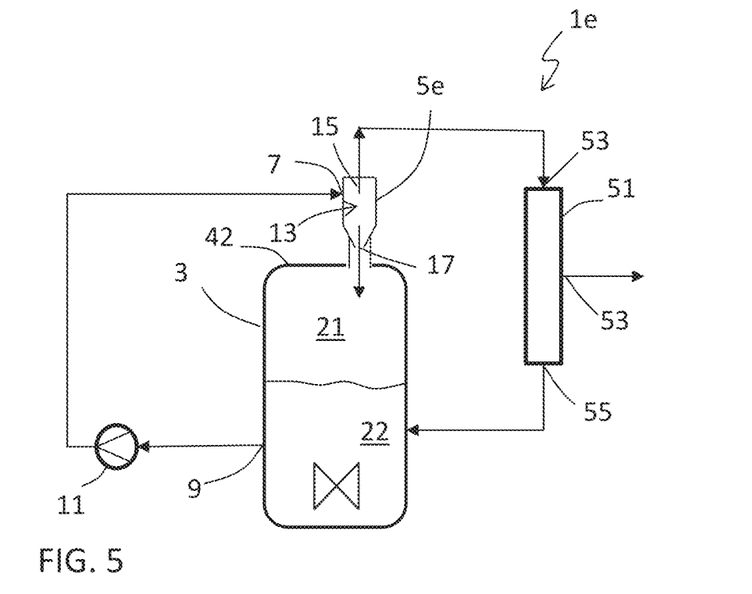
FIG. 5 shows schematically a bioreactor system according to another embodiment of the invention.

In some embodiments of the invention, for example as shown in FIGS. 1, 4 and 5, the bottom outlet 17 of the hydrocyclone 5a; 5d, 5d'; 5e is provided pointing or extending into the bioreactor 3 whereby the hydrocyclone is integrated in a side wall 42 of the bioreactor 3.

The bioreactor 3 can be a flexible bag and the hydrocyclone can be produced from plastic. Hereby the bioreactor 3, the at least one hydrocyclone 5a; 5b; 5d, 5d'; 5e and a single-use part of the pump 11 and fluid connections can be provided as single-use components of the bioreactor system, optionally as a presterilized single-use package. The single-use package can be sterilized by for example gamma radiation.

Figure 3:
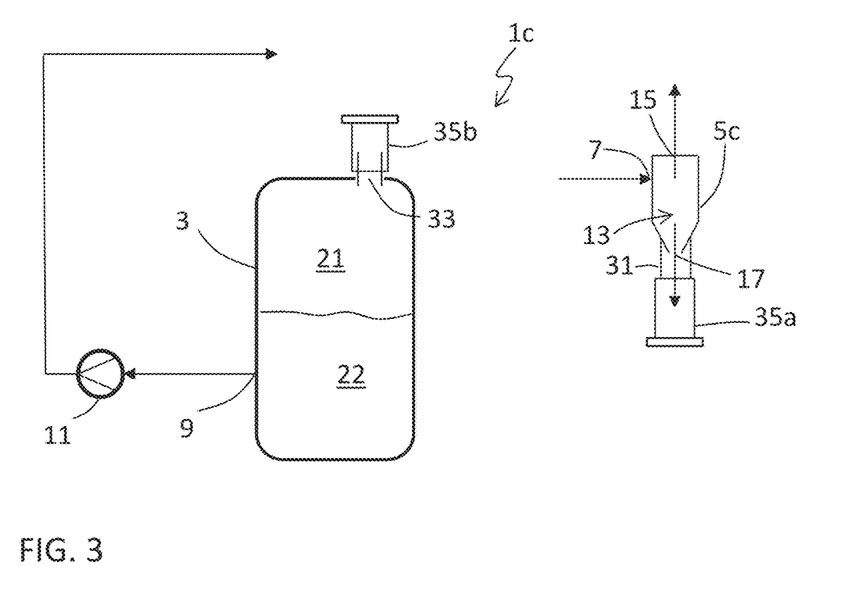
FIG. 3 shows schematically a hydrocyclone according to one embodiment of the invention and a bioreactor to which the hydrocyclone is configured to be connected.

In FIG. 3 a bioreactor system 1c is shown where the bioreactor 3 is provided with an inlet connection 33 which suitably is provided with an aseptic connection 35b. In this embodiment of the invention the hydrocyclone 5c is provided as a separate part which can be connected to the inlet 33 of the bioreactor 3. The hydrocyclone 5c comprises a cell culture inlet 7 which is configured to be connected to a cell culture 22 in the bioreactor 3 via a pump 11, whereby cell culture from the bioreactor can be transferred to the hydrocyclone 5c. The hydrocyclone comprises further a hydrocyclone separation part 13 into which cell culture can be introduced from the cell culture inlet 7, a top outlet 15 through which a part of the cell culture with decreased cell concentration can be transferred after separation in the hydrocyclone separation part 13 and a bottom outlet 17 through which a part of the cell culture with increased cell concentration can be transferred after separation in the hydrocyclone separation part 13. The hydrocyclone 5c comprises furthermore according to the invention a connection device 31 which is provided to surround the bottom outlet 17 of the hydrocyclone 5c leaving a free space around it such that a cell culture transferred out form the bottom outlet 17 is allowed to freely discharge, such as spray out around the bottom outlet 17, wherein said connection device 31 is configured to be connected to an inlet 33 of the bioreactor. The connection device 31 can in one embodiment of the invention be an aseptic connector itself. However, in the embodiment shown in FIG. 3 an aseptic connector 35a is provided to the connection device 31. Hereby aseptic connection to the inlet 33 of the bioreactor 3 can be provided.

As described above the connection device 31 can be a tubular part connected to the hydrocyclone symmetrically around the bottom outlet 17, wherein said tubular part leaves a free space around the bottom outlet for allowing free discharge around the bottom outlet. The tubular part can for example have an inner diameter of at least 2 cm as discussed above. Said connection device 31 can comprise a bellows or a telescope connection.

Said hydrocyclone can be produced from plastic and can be a pre-sterilized single-use component.

In FIG. 4 a bioreactor system 1d according to one embodiment of the invention is shown schematically. This bioreactor system 1d comprises two connected hydrocyclones 5d, 5d'. The top outlet 15 of a first hydrocyclone 5d is connected to a cell culture inlet 7 of a second hydrocyclone 5d'. Both of the hydrocyclones 5d, 5d' are positioned such that their bottom outlets 17 are provided in connection with the headspace 21 in the bioreactor 3 when the bioreactor system is used for culturing cells. Hereby any possible cells which are removed through the top outlet 15 of the first hydrocyclone 5d can be separated in the second hydrocyclone 5d' to the bottom outlet 17 of the second hydrocyclone 5d' and an overall separation efficiency will be increased, i.e. a waste of cells will be decreased. In another embodiment of the invention more than two hydrocyclones can be connected in a bioreactor system. For example two or more hydrocyclones, such as 5 hydrocyclones, can be connected in parallel to the cell culture of a bioreactor in a first stage whereby the flow out from the top outlets 15 of these parallel connected hydrocyclones can be transferred to another hydrocyclone for further separation and return of cells to the bioreactor.

In FIG. 5 a bioreactor system 1e according to another embodiment of the invention is shown schematically. This bioreactor system 1e comprises one hydrocyclone 5e and another type of separation device, such as a hollow fiber filter 51. Instead of a hollow fiber filter it could be an acoustic settler, flat sheet filter or NF filter. The hollow fiber filter 51 comprises an inlet 53 connected to the top outlet 15 of the hydrocyclone 5e and a retentate outlet 55 connected to the bioreactor 3 and a permeate outlet 57 configured for transferring a part of the cell culture with decreased cell concentration out from the bioreactor system 1e when the bioreactor system is used for culturing cells. Hereby any possibly remaining cells in the flow out from the top outlet 15 of the hydrocyclone 5e can be filtered back into the bioreactor 3 by the hollow fiber filter 51 and a separation efficiency will be increased.

Figure 6:
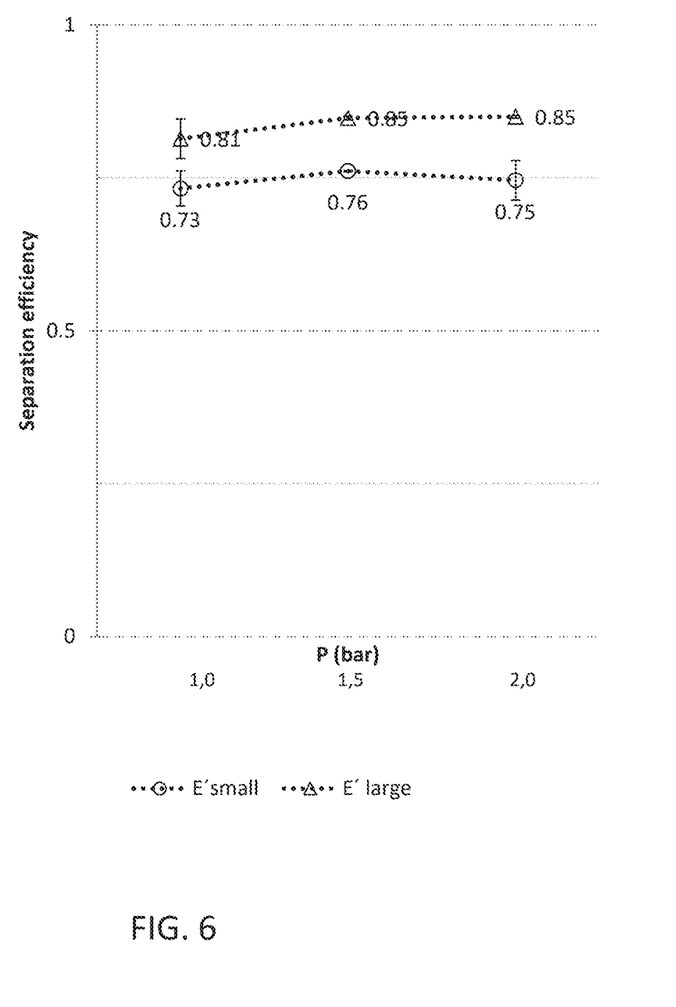
FIG. 6 is a diagram showing separation efficiency for a hydrocyclone with a wide bottom outlet connection according to the invention and separation efficiency for a hydrocyclone with a narrow bottom outlet connection.

FIG. 6 shows results from an experiment measuring separation efficiencies of a hydrocyclone with a wide bottom outlet connection according to the invention and separation efficiencies of a hydrocyclone with a narrow bottom outlet connection, i.e. a normal tube connection. In this experiment the wide bottom outlet connection had a diameter of 1" and the narrow bottom outlet connection had a diameter of ⅜". Furthermore the used cell culture was Superdex™ 200 beads (34 μm) at 1E6/mL. In FIG. 6 the separation efficiencies for different pressures were measured and it is clearly shown that the separation efficiency was higher for the large bottom outlet connection than for the small bottom outlet connection for all pressures.

Hereby this experiment clearly shows that a wide (large) connection to the bottom outlet 17 of the hydrocyclone 5 will increase separation efficiency of the hydrocyclone.

Figure 7:
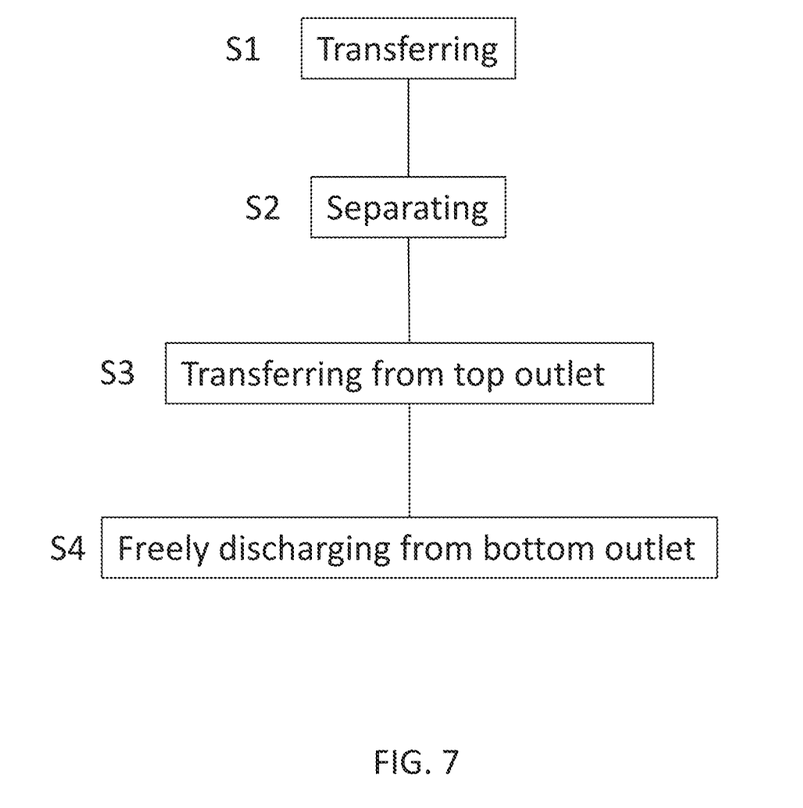
FIG. 7 is a flow chart showing the method steps according to one embodiment of the invention.

FIG. 7 is a flow chart showing the method steps according to one embodiment of the invention. The steps are described in order below:

S1: Transferring a part of a cell culture provided in the bioreactor 3 to a cell culture inlet 7 of the hydrocyclone 5a; 5b; 5c; 5d, 5d'; 5e.

S2: Separating the cell culture in a hydrocyclone separation part 13 of the hydrocyclone into which hydrocyclone separation part the cell culture is introduced from the cell culture inlet 7, whereby the cell culture is separated into one part of the cell culture with decreased cell concentration and one part of the cell culture with increased cell concentration.

S3: Transferring the part of the cell culture with decreased cell concentration out from the hydrocyclone through a top outlet 15 of the hydrocyclone; and S4: Freely discharging the part of the cell culture with increased cell concentration out from the hydrocyclone through a bottom outlet 17 of the hydrocyclone, wherein said bottom outlet 17 of the hydrocyclone 5a; 5b; 5c; 5d, 5d'; 5e is provided in connection with a headspace 21 in the bioreactor 3 and wherein said bottom outlet 17 is provided such that the bottom outlet has a free space around it such that the cell culture transferred out form the bottom outlet is allowed to freely discharge around the bottom outlet, such as spraying out around the bottom outlet.

As described above in relation to FIGS. 4 and 5 the part of the cell culture with decreased cell concentration which is transferred out from the hydrocyclone through the top outlet 15 may be transferred for further separation in either another hydrocyclone 5d' or another type of separation device such as a hollow fiber filter 51. After this further separation any remaining cells can be returned to the bioreactor 3.

The method and system according to the invention can both be used for perfusion mode and for a final harvest step where the harvest is removed through the at least one hydrocyclone and the cells are concentrated in the bioreactor (without the addition of new cell culture media as during perfusion mode) and then the concentrated cell suspension is washed in a diafiltering step.

The invention claimed is:

1. A hydrocyclone configured to be connected to a bioreactor, said hydrocyclone comprising:
a cell culture inlet which is configured to be connected to a cell culture in the bioreactor via a pump, whereby cell culture from the bioreactor can be transferred to the hydrocyclone;
a hydrocyclone separation part into which cell culture can be introduced from the cell culture inlet,
a top outlet through which a part of the cell culture with decreased cell concentration can be transferred after separation in the hydrocyclone separation part;
a bottom outlet through which a part of the cell culture with increased cell concentration can be transferred after separation in the hydrocyclone separation part; and
a connection device which is provided to surround the bottom outlet of the hydrocyclone leaving a free space around it such that a cell culture transferred out form the bottom outlet is allowed to freely discharge around the bottom outlet, wherein said connection device is configured to be connected to an inlet of the bioreactor;
wherein said connection device is a tubular part connected to the hydrocyclone symmetrically around the bottom outlet, wherein said tubular part has a diameter of at least 2 cm; and
wherein said connection device comprises an aseptic connector and wherein said hydrocyclone is produced from plastic and is a pre-sterilized single-use component.

2. The hydrocyclone according to claim 1, wherein said connection device comprises a bellows or a telescope connection.

3. A bioreactor system for culturing cells, comprising:
at least one bioreactor; and
at least one hydrocyclone comprising:
a cell culture inlet which is connected to a cell culture outlet of the bioreactor via a pump, whereby a cell culture from the bioreactor can be transferred to the hydrocyclone when a cell culture is provided in the bioreactor;
a hydrocyclone separation part into which cell culture can be introduced from the cell culture inlet,
a top outlet through which a part of the cell culture with decreased cell concentration can be transferred after separation in the hydrocyclone separation part; and
a bottom outlet through which a part of the cell culture with increased cell concentration can be transferred after separation in the hydrocyclone separation part; and
a connection device which is provided to surround the bottom outlet of the hydrocyclone leaving a free space around it such that the cell culture transferred out from the bottom outlet is allowed to freely discharge around the bottom outlet, wherein said connection device comprises an aseptic connector, and wherein said connection device is a tubular part connected to the hydrocyclone symmetrically around the bottom outlet, wherein said tubular part has an inner diameter of at least 2 cm, and wherein said hydrocyclone is produced from plastic and is a pre-sterilized single-use component,
wherein said bottom outlet of the hydrocyclone is provided in a position such that when the bioreactor system is used for culturing cells the bottom outlet is in connection with a headspace of the bioreactor and wherein said bottom outlet is provided such that the bottom outlet has a free space around it such that a cell culture transferred out form the bottom outlet is allowed to freely discharge around the bottom outlet.

4. The bioreactor system according to claim 3, wherein said bottom outlet is provided such that the bottom outlet has a free space of at least 1 cm radially around it.

5. The bioreactor system according to claim 3, wherein the hydrocyclone is integrated with the bioreactor such that the bottom outlet of the hydrocyclone is provided directly in the headspace of the bioreactor when the bioreactor system is used for culturing cells.

6. The bioreactor system according to claim 3, wherein the bioreactor is a flexible bag and the hydrocyclone is produced from plastic and wherein at least the bioreactor and a single-use part of the pump are provided as single-use components of the bioreactor system, optionally as a pre-sterilized single-use package.

7. The bioreactor system according to claim 3, wherein the hydrocyclone is provided inside the bioreactor and the top outlet of the hydrocyclone is connected to a port in a wall of the bioreactor.

8. The bioreactor system according to claim 3, wherein the bottom outlet of the hydrocyclone is provided pointing into the bioreactor whereby the hydrocyclone is integrated in a side wall of the bioreactor.

9. The bioreactor system according to claim 3, wherein the bioreactor system comprises at least two connected hydrocyclones, wherein the top outlet(s) of one or more first hydrocyclone(s) is connected to a cell culture inlet of a second hydrocyclone and wherein all the hydrocyclones are positioned such that their bottom outlets are provided in connection with the headspace in the bioreactor when the bioreactor system is used for culturing cells.

10. The bioreactor system according to claim 3, wherein the bioreactor system further comprises a hollow fiber filter comprising an inlet connected to the top outlet of the hydrocyclone and a retentate outlet connected to the bioreactor and a permeate outlet configured for transferring a part of the cell culture with decreased cell concentration out from the bioreactor system when the bioreactor system is used for culturing cells.

* * * * *